United States Patent [19]

Archer

[11] 4,409,841

[45] Oct. 18, 1983

[54] FATIGUE DAMAGE INDICATORS

[75] Inventor: Michel Archer, La Celle-St. Cloud, France

[73] Assignee: Societe Anonyme: Stas Societe Technique d'Accessories Specialises, Sartrouville, France

[21] Appl. No.: 221,212

[22] Filed: Dec. 30, 1980

[30] Foreign Application Priority Data

Jan. 3, 1980 [FR] France .............................. 80 00342
Jul. 31, 1980 [FR] France .............................. 80 17225
Dec. 12, 1980 [FR] France .............................. 80 26727

[51] Int. Cl.³ ...................... G01B 11/20; G01N 3/00; G01N 19/00; G01L 5/00
[52] U.S. Cl. ...................................... 73/762; 73/810; 73/760; 73/799; 116/212
[58] Field of Search ................. 73/799, 787, 760, 810, 73/762; 116/212

[56] References Cited

U.S. PATENT DOCUMENTS

| | | | |
|---|---|---|---|
| 2,920,480 | 1/1960 | Haas | 73/787 |
| 3,244,137 | 4/1966 | Garvey | 116/212 |
| 3,572,091 | 3/1971 | McFarland | 73/760 |
| 3,774,443 | 11/1973 | Green et al. | 73/799 |
| 3,786,679 | 1/1974 | Crites | 73/787 |
| 3,994,598 | 11/1976 | Reytblatt | 73/762 X |
| 4,107,980 | 8/1978 | Crane et al. | 73/799 |
| 4,164,874 | 8/1979 | Cassatt et al. | 73/799 |
| 4,278,043 | 7/1981 | Heath | 116/212 X |
| 4,322,981 | 4/1982 | Radwill | 73/810 |

FOREIGN PATENT DOCUMENTS

| | | | |
|---|---|---|---|
| 54-45191 | 4/1979 | Japan | 116/212 |
| 147834 | 9/1960 | U.S.S.R. | 73/810 |

OTHER PUBLICATIONS

Measurement of Crack Growth in a Notch; by Nicholson, Journal of Physics E: Scientific Instruments, vol. 7, 1974, pp. 741–743.

Strength Testing with Fatigue Crack; by Neshpor et al., Ind. Lab, (USA) vol. 43, No. 1, Jan. 1977 from Zauodskaya Laboratorya.

Notched Strip Shows Fatigue Damage, Jul. 1981 of Machine Design.

Structural Evolution During Fatigue, by Guy Henry and Dietrich Horstmann, Max-Planck Inst. (Date Unknown).

A Surface-Coating Technique for Monitoring Stress . . . . Cracks, by Sorel, NDI International, Oct. 1981, pp. 281–284.

Fatigue Crack Propagation from Crack Arrays, by Shaw, W. J. D. and Le May, I., Univ. of Saskat. 15th Inter. Conf. at Cannes, 1981.

Primary Examiner—Stephen A. Kreitman
Assistant Examiner—David V. Carlson
Attorney, Agent, or Firm—Karl F. Ross; Herbert Dubno

[57] ABSTRACT

A fatigue damage indicator includes a thin plate mounted between or integral with two members to which a stress is to be applied, the disposition of the two members being such that the thin plate is stressed in shear.

Slots extending in the direction of the applied stress may be provided to ensure that cracks formed by fatigue stress propagate in a desired direction and the crack propagation is designed to ensure that a part of the plate becomes detached or is bent substantially away.

13 Claims, 30 Drawing Figures

FATIGUE DAMAGE INDICATORS

FIELD OF THE INVENTION

This invention relates to fatigue damage indicators

BACKGROUND OF THE INVENTION

The repeated use of a mechanical part causes fatigue damage and the part may fracture although it is submitted to a normal stress, the working load not exceeding the load for which the part was intended.

Unfortunately, the fatigue damage of a part is not visible and there does not exist, at the present time, any simple means for determining the fatigue state, which can be the source of serious accidents.

U.S. Pat. No. 4,164,874 describes a fatigue damage indicator comprising two thick members, which are spaced from one another and interconnected by a thin plate provided with a slot, these two members being incorporated in the part or fixed to the latter in such a manner as to be displaced with respect to one another in a plane which is parallel to the plane of the slot.

When the part becomes fatigued, a crack is formed starting from the slot. It is possible to measure the progress of the crack, for example with the aid of a scale engraved on the indicator. But the crack is scarcely visible and the fatigue of the part may well be overlooked as a result.

OBJECTS OF THE INVENTION

An object of the invention is the provision of an indicator of the above described type, but which enables the user to realize immediately when a part becomes fatigued.

It is a further object of the invention to provide a fatigue damage indicator which can readily be incorporated in a part or structure liable to be subjected to repeated stresses or secured on such a part or structure and which enables instant knowledge that a predetermined fatigue stress has been reached.

SUMMARY OF THE INVENTION

According to the present invention there is provided a fatigue damage indicator, a first comparatively thick member, a second comparatively thick member, and a comparatively thin plate interconnecting the first and second thick members so disposed that stresses applied to the first and second members are applied to the thin plate as a shear stress, and having two slots each extending in the direction of applied stress to the first and second members, a predetermined fatigue stress serving to crack the comparatively thin plate starting from the slots and displacing a part thereof from its initial location relative to the first and second members.

The propogation of cracks in the thin plate depends on displacements which are imposed on the fatigue indicator by the part to be monitored and, as a consequence, stresses applied to that part. Thus, the cracks play the role of a memory and register all the actions to which the part is subjected in service. This memory is selective in as far as substantial stress causes more rapid progression of the crack in the plate than a weak stress.

The two thick or massive members and the thin plate can be constituted by a comon part which is provided with a blind hole on its two opposite faces, the two holes being co-axial so that their bottoms are separated by the plate, and having dimensions such that the plate will be the sole connection between the two parts.

The plate is preferably generally circular. It can be provided with a central hole. It may comprise a single slot or two slots opposed to one another in the direction of relative displacement of the two thick members. The plate may be plane or bowed. It may also comprise supplementary holes or recesses providing the guidance for the eventual cracks. It may be connected to each thick member by a machined fillet. The plate may be of variable thickness.

The blind end of the slot or slots may be planar or convex.

Grooves can be formed on at least one face of the thin plate, starting at the blind ends of the slot. These grooves constitute zones of weakness so that the cracks will form at the region of the grooves and thus follow a predetermined direction. It is also possible to provide notches traversing the plate and starting at blind ends of the slots. Again, these notches constitute zones of stress concentration in order to better control the initiation of the cracks.

Experience shows that the reliability of fatigue indicators in accordance with the invention depends to some extent upon the dimensions of these notches and of the stress concentration caused by the notches. There is, as a result, some advantage if the width of the notch is substantially nil, the front face of this notch being more inclined with respect to the plane of the thin plate.

The thin plate may be separate from the thicker members to which it is secured for example by screws or bolts, by rivet pins or by welding.

The slot or slots may be enlarged at the region of their blind end. They may also have the shape of a segment of a circle and outwardly terminate at a part of constant length or again have the shape of a truncated circular section.

The fatigue indicator may comprise two slots opposed to one another in the direction of relative displacement of the two thick members. In such a construction the two slots may be off-set, the one in relation to the other, over the whole or a part of their lengths, with respect to an axis parallel to the direction of stress applied to the associated thick members.

The angle at the blind end of the slot or slots which is subjected to tension when the part is working is advantageously obtuse, although the other angle which is subjected to compression is a right angle or an acute angle.

Experience shows that the cracks in the plate begin more rapidly when the part being monitored is subjected to a tensile force than when it is subjected to a compression force. Since, moreover, cracks form more readily at an acute angle than an obtuse angle, it is possible substantially to balance the rate of initiation of cracks at two angles at the slot or slots.

When the cracks are formed in the thin plate starting from angles at the slot, and are completed by reaching the opposite edge of the plate or cracks starting from angles at a second slot opposed to the first, it may be that as the result of rubbing of the edges of the cracks, the detached part of the plate will not separate materially from it and that thus the fatigue would not be indicated.

For greater safety, the blind end of the slot may be provided with an upstanding hook extending out of the plane of the thin plate and to which is secured one of the ends of a tension spring, its other end being secured to the plate or to the part of which the fatigue damage is to be monitored. Under these conditions, when the part is fatigued and the cracks have propagated sufficiently, the spring ensures the ejection of the detached part of the plate or at least displaces it, which enables it to become apparent without difficulty that the part is fatigued.

When the part to be monitored has a zone submitted to a substantially uniform and uniaxial field of stresses, the two thick members are advantageously secured to the surface of the part in a direction forming an angle of 25° to 35° with the direction of the main applied stress.

When the part is working, the relative displacement of the two portions of the plate situated on either side of the axis of the slot is practically a pure sliding movement.

It is thus possible to produce a fatigue indicator usable in a given part without it being necessary to substantially modify the part.

The optimum inclination has a value Arc tg $\sqrt{\mu}$, $\mu$ being the poisson coefficient of the material constituting the plate. This angle has a value of 29° in the case of steel, the poisson coefficient being about 0.3.

BRIEF DESCRIPTION OF THE DRAWING

Fatigue damage indicators embodying the invention will now be described, by way of example, with reference to the accompanying diagrammatic drawings in which.

SPECIFIC DESCRIPTION

Figures 1, 2:
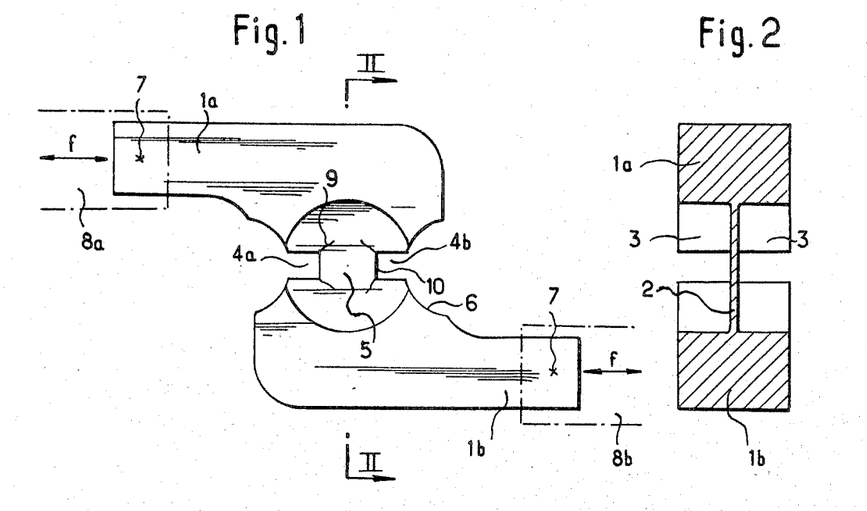
FIG. 1 is a side elevation of a first embodiment of a fatigue indicator in accordance with the invention.
FIG. 2 is a section taken on the line II—II of FIG. 1.

As is illustrated in FIG. 1, the fatigue damage indicator embodying the invention comprises two comparatively thick, or massive, elongated members 1a, 1b, which lie parallel to one another and are interconnected by a comparatively thin plate 2, integral which the members 1a, 1b or secured to the latter.

This plate extends transversely with respect to the length direction of the members 1a, 1b and is situated in the common longitudinal median plane of the latter. In other words, a blind-hole 3 is formed in each lateral face of the assembly of members 1a, 1b, the bottom surfaces of these two holes being separated from one another by the thin plate 2. In the example illustrated these bottom surfaces are planar so that the plate is defined by two parallel plane faces, but they may be bowed or arcuate.

The plate 2 is generally circular and is provided, in the direction of its diameter, parallel to the length of the members 1a, 1b, with two slots 4a and 4b which open outwardly and between which lies an interrupted part 5 of the plate providing connection between the two members 1a, 1b. These members extend up to the ends of the slots 4a, 4b through the intermediary of opposed concave edges 6

The two members 1a, 1b are fixed preferably at their free ends, as indicated at 7, to two portions 8a and 8b (dot-dash lines) of a common part and move substantially in the length direction of the members 1a, 1b when the part is working, as is indicated diagrammatically by the arrows f; they may also be integral with two portions of the part. The direction of relative displacement of the parts 8a, 8b is substantially parallel to the plane of the plate 2.

During use of the part, the two members 1a, 1b move together in the direction of the arrows f, while exerting a shear stress on the plate 2, at the region of the part 5. When the part being monitored has been subjected to a certain number of working cycles, the part 5 cracks as indicated at 9. These cracks start at the bases of the slots 4a, 4b and progressively encompass the part 5, so that the latter finally detaches itself at the end of a certain number of cycles, which indicates that the part is fatigued and must be scrapped.

In the preceding description, it has been indicated that the members 1a, 1b were elongated, but this is not necessary. The members may be limited to the part in the zone of the plate 5 by being secured directly to the parts 8a, 8b of the part to be monitored, for example at points disposed in the region of the part 5 of the plate.

The bases 10 of the slots 4a, 4b may be planar, as shown in FIG. 1. They may also be convex as shown in FIG. 3.

It is advantageous that the slots 4a, 4b should terminate at acute angles which enable, owing to the stress concentrations which are a result thereof, a determination of the initiation point of the cracks.

Figures 3, 4:
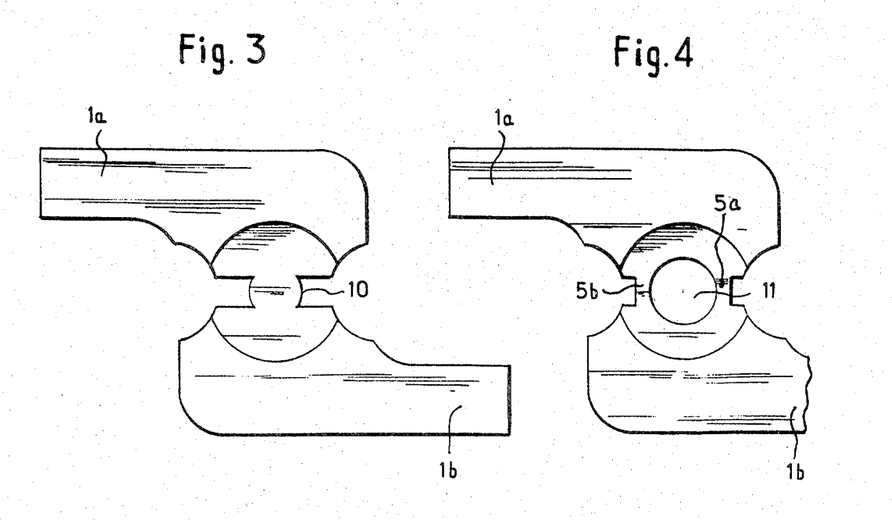
FIGS. 3–5 and 7 and 8 show as side elevations, modifications of the fatigue damage indicator of FIGS. 1 and 2.

A hole 11 may possibly be provided at the center of the part 5, as can be seen in the modification of FIG. 4. In this modification, the one and/or the other of the parts 5a, 5b lying between the bottom of the slots and the hole become detached when the part is fatigued.

Figure 5:
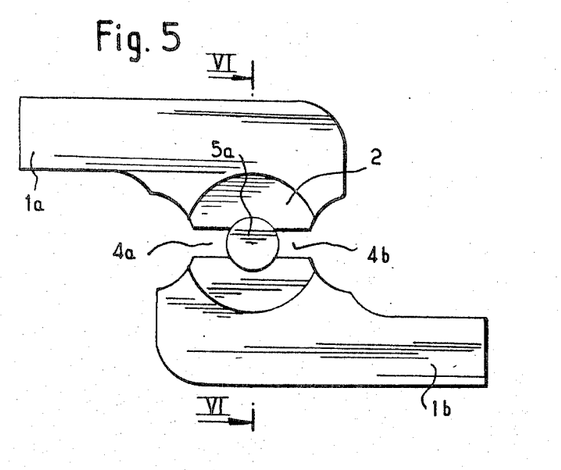
Figure 6:
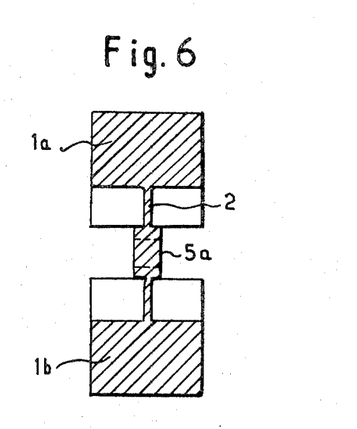
FIG. 6 is a section taken on the line VI—VI of FIG. 5.

The plate can be of variable thickness. In particular, it may, as indicated in FIGS. 5 and 6, be reinforced at its center 5a in such a manner as further to concentrate the stresses on the thinner adjacent part.

Figure 7:
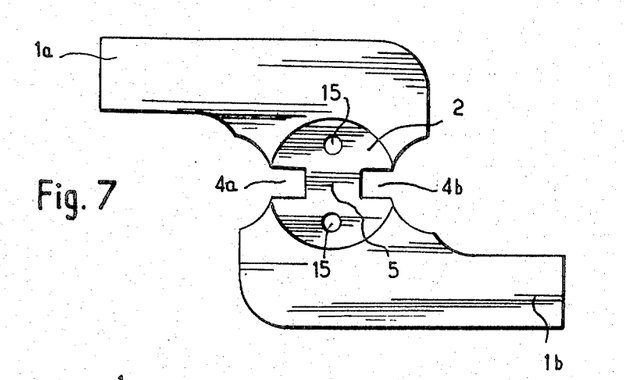
Figure 8:
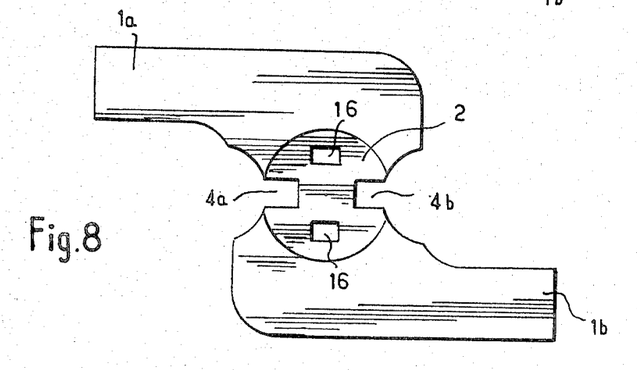

A supplementary recess can be formed in the plate in such a manner as better to guide the propagation of the cracks. This supplementary recess can take the form of two circular holes 15 as in FIG. 7, or two rectangular holes 16 as in FIG. 8. In FIGS. 7 and 8 the holes 15 and 16 are disposed to lie on a diameter of the plate perpendicular to that of the slots 4a, 4b.

Figure 9:
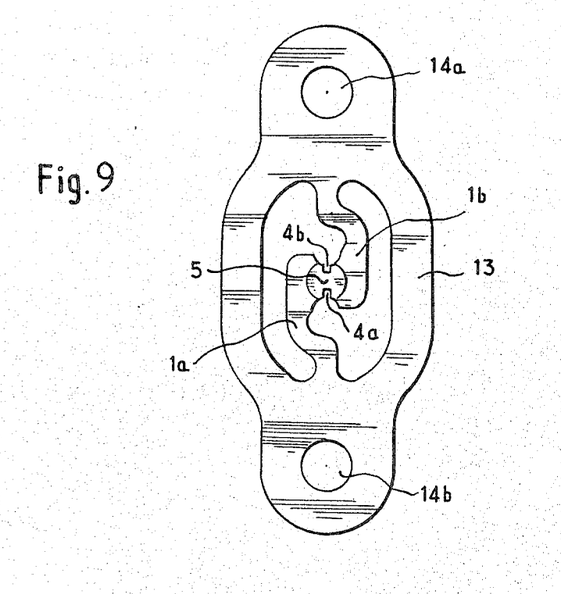
FIG. 9 shows a fatigue damage indicator incorporated in a hoisting ring.

The fatigue indicator may be incorporated in the part to be monitored in place of being fixed to the latter. Thus in FIG. 9, an elongated hoisting ring 13 is provided at its ends with two attachment points 14a, 14b. The fatigue damage indicator is disposed within the ring, its members 1a, 1b which are aligned in the longitudinal direction of the ring, are connected at the internal periphery of the ring. When the ring is placed in tension, through the intermediary of the securing points 14a, 14b (or in compression), the two membera 1a, 1b become further spaced apart (or approach one another). The slots 4a, 4b are aligned with the longitudinal direction of the ring and disposed in the median plane of the latter. The part 5 of the indicator is thus subjected to a shearing stress when a tensile or a compressive stress is exerted on the two points 14a, 14b of the ring.

Figures 10, 11, 12, 13:
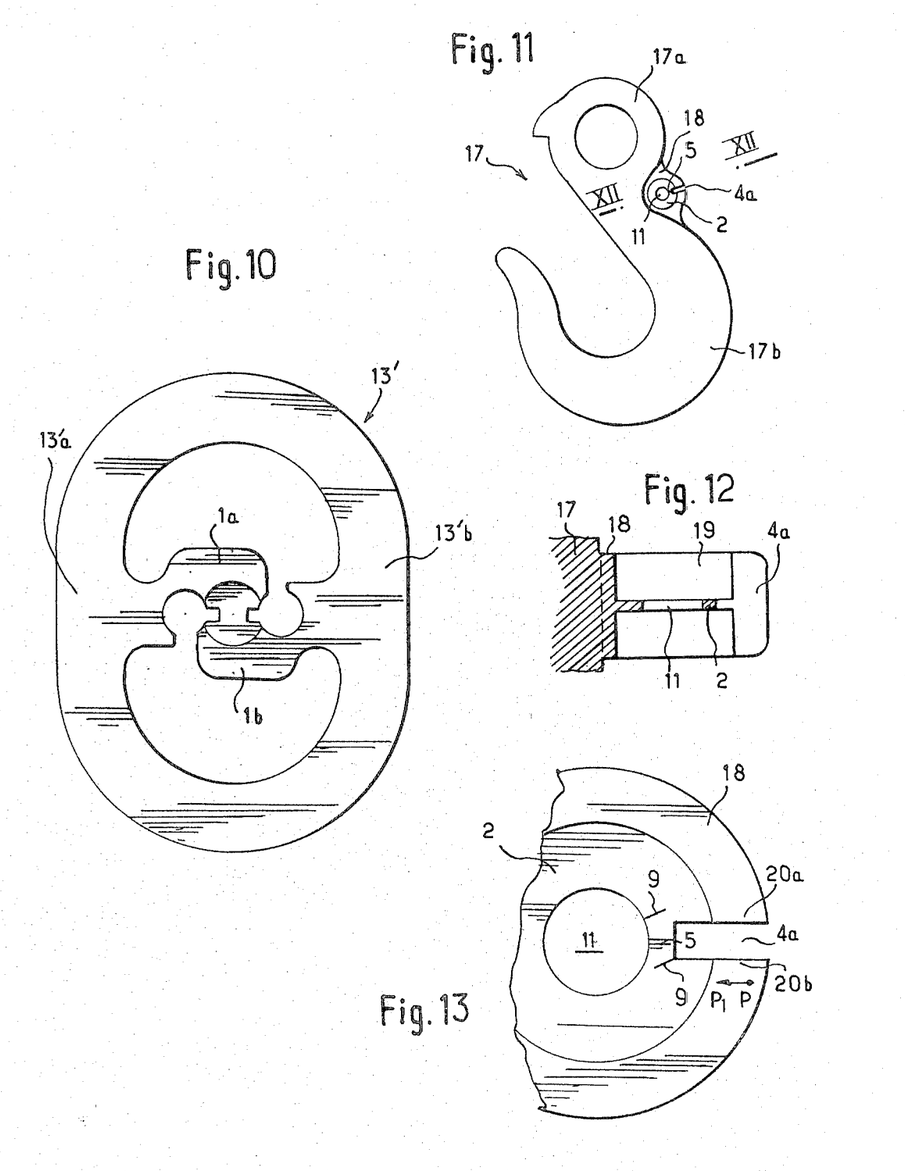
FIG. 10 shows another fatigue damage indicator incorporated in another hoisting ring.
FIG. 11 shows a fatigue damage indicator as incorporated in a hook.
FIG. 12 is a section, drawn to an enlarged scale, taken on the line XII—XII of FIG. 11.
FIG. 13 shows in elevation, drawn to an enlarged scale, the plate of the hook and cracks which form therein.

FIG. 10 also shows a ring 13' provided with a fatigue indicator, but the indicator is disposed perpendicularly to the direction of the tensile force (or of the compressive force) that is to say that the members 1a, 1b are oriented transversely with respect to the length direction of the ring.

When the ring is placed under tension (or compression) it deforms and its two branches 13'a, 13'b approach one another or become further spaced from one another, while entraining in their movements the members 1a, 1b of the fatigue indicator and imposing thereon shear movement.

The fatigue indicator can be incorporated in a hook (FIG. 11 to FIG. 13). The hook comprises a boss 18, on its outer face, at the junction between an eye portion 17a and a body portion 17b. A hole 19 is formed in the boss traversed substantially at its center with a hole 11. A slot 4a is formed in the boss which extends within the plate 2, substantially in the median plane of the boss 18. The position of the slot 4a and its orientation with respect to the boss enables relative displacement of the two walls of the slot substantially parallel to the walls.

In a particular embodiment of the invention, which gave a good performance, the plate had a thickness of 1 mm. and its central hole a radius of 3.5 mm; the slot had a thickness of 1.6 mm. and extended within the plate up to 1.5 mm. of the edge of the hole 11. These dimensions correspond to a hook loading of two tonnes of overall length of 162.5 mm and of a thickness of 14 mm., of which the diameter of the eye is 30 mm. and the diameter of the seat 45 mm.

During use of the hook it tends to open, which deforms the boss 18 and the plate 2; the two longitudinal portions 20a, 20b of the slot move substantially parallel to one another. The tip of the portion 20b tends to move toward $P_1$ if it is assumed that the portion 20a is fixed. When the hook has been subjected to a certain number of loading cycles, the part 5 of the plate 2, which lies at the end of the slot 4a, fractures at 9. These fractures progressively surround the said part 5 so that it ends by detaching itself on completion of a certain number of cycles. This number of cycles itself depends on the position of the hole and of the plate 2, with respect to the hook and the boss, and the thickness of the plate, upon the width and the depth of the slot.

It should be noted that the plate 2 is located at a zone where it does not interfere with the operation of the hook and the plate is protected against shocks and abrasion. Since boss 18 does not normally exist as a part of the hook, the crack or the fracture of the plate will not weaken the hook in itself.

Figure 14:
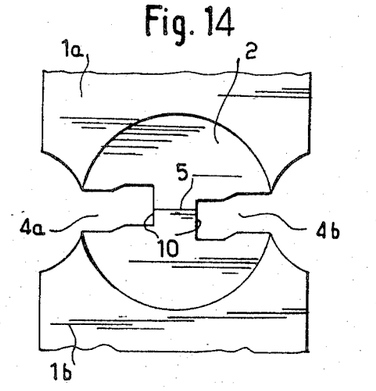
FIG. 14 is an elevation of another embodiment of the indicator.

The slots 4a, 4b, instead of being disposed on a common longitudinal axis passing through the center of the plate, can be offset with respect to each other, partially or completely. In the embodiment of FIG. 14, the other parts of the slots are disposed on a common longitudinal axis, but their blind ends 10 are offset with respect to each other, on one side and on the other of this longitudinal axis.

Figure 15:
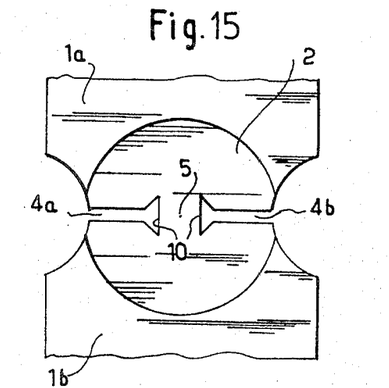
FIGS. 15 and 16 are similar views to that of FIG. 14 of two other embodiments.

The width of the slots 4a, 4b need not be the same over the whole length of the slots. In FIG. 15 the slots 4a, 4b are enlarged at their blind end portion 10.

Figure 16:
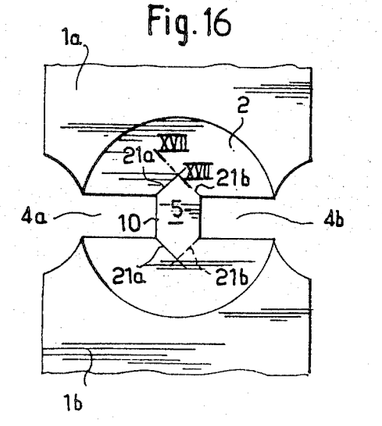
Figure 17:
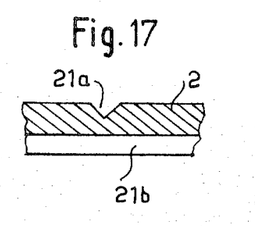
FIG. 17 is a transverse section taken on the line XVII—XVII of FIG. 16.

Grooves 21a, 21b can be formed in the central part 5 of the plate, starting from the blind ends of the slots 4a, 4b. In the embodiment of FIGS. 16 and 17, the grooves 21a which start from the blind ends 10 of the slot 4a are provided on one of the faces of the plate while the grooves 21b which start from the blind ends 10 of the slot 4b and are formed on the opposite face of the plate.

Figure 18:
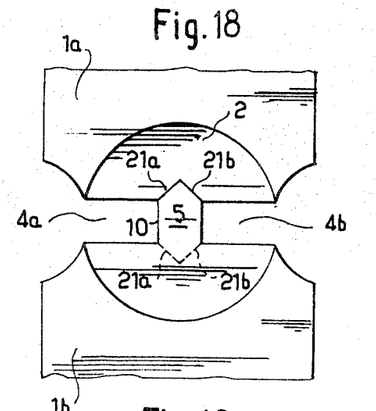
FIGS. 18–20 are elevations of three further embodiments of the fatigue indicator.

In the embodiment of FIG. 18 the grooves 21a are formed with one on one of the faces of the plate and the other on its other face. Similarly the grooves 21b are formed on alternate faces; the two grooves 21a and 21b which are provided in the same face of the plate, extending from the blind ends 10 are disposed at the same side with respect to the axis of the slots.

Figure 19:
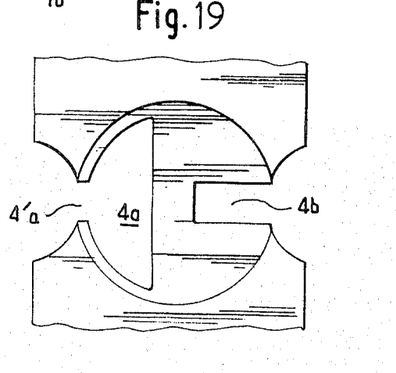
Figure 20:
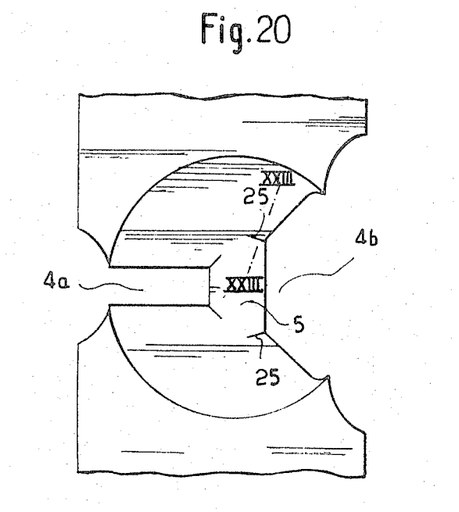

In the embodiment of FIG. 19, the slots 4a, 4b are completely different from one another. The slot 4b has a constant width while the slot 4a is in the form of a segment of a circle and opens outwardly at one part 4'a to a width approximately equal to that of the slot 4b.

In the embodiments of FIGS. 20 to 23, the slots 4a, 4b are again completely different from one another. The slot 4b is in the form of a truncated sector. The plate 2 comprises, in one of its faces, notches 25 which start from each end of the blind inner end 10 of the slots 4a, 4b. These notches are machined by any procedure enabling the production of as high a finish as possible, such as electro-erosion, electro-erosion by wire, cutting by laser, or cutting by electron beam.

Figure 21:
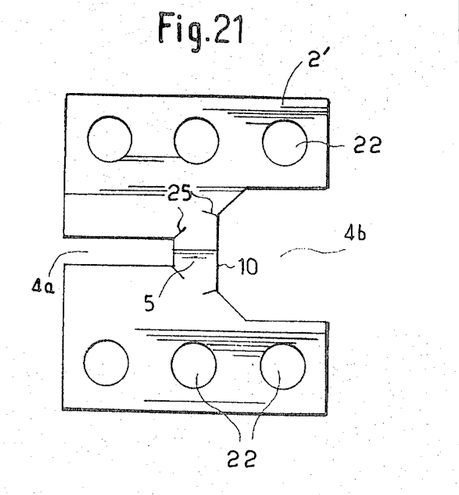
FIG. 21 is an elevational view of a plate showing another embodiment of the indicator.

FIG. 21 shows a fatigue indicator in which the thin plate 2' is independent of the thick members 1a, 1b and can be fixed to the latter by pins traversing holes 22 provided in the plate. This fatigue indicator, produced by starting from a separate plate, can be associated with any of the possible forms of the central part 5 and of the slots 4a, 4b which have been described hereinbefore. In the particular embodiment of FIG. 21, the slots 4a and 4b have the same lengths but different widths. This plate 2' comprises on one of its faces notches 25 which start from corners of the blind ends 10 of the slots 4a, 4b.

Figure 22:
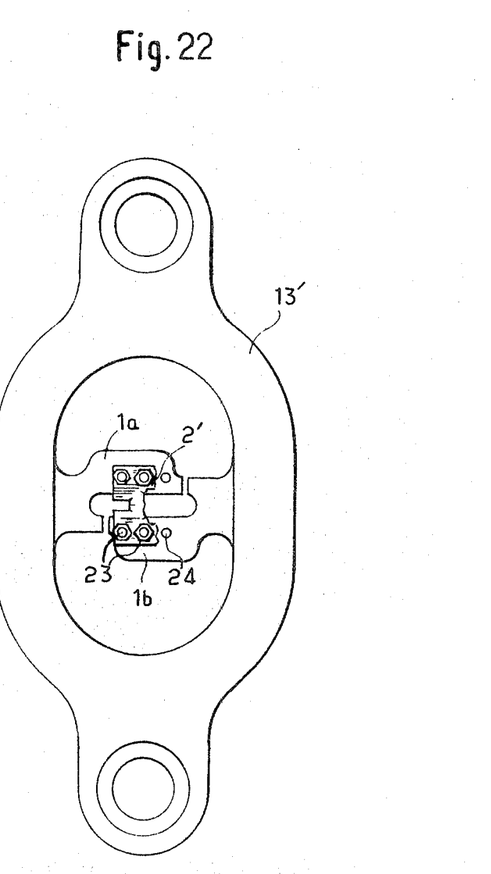
FIG. 22 shows in elevation a hoisting ring provided with a fatigue indicator comprising the plate of FIG. 21.
Figure 23:
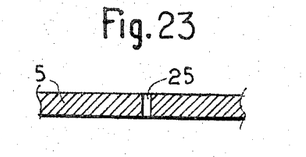
FIG. 23 is a transverse section taken on the line XXIII—XXIII of FIG. 20.

FIG. 22 shows a thin plate 2' secured in a hoisting ring similar to that shown in FIG. 10. The plate is secured on the part 1a, 1b of the ring by screws pins 23, or rivets which traverse the holes 22 of the plate and are screwed into tapped bases 24 of the said parts 1a, 1b, or by any other means, for example by electrical spot welding, by welding or laser or by welding with the aid of an electron beam.

Figure 24:
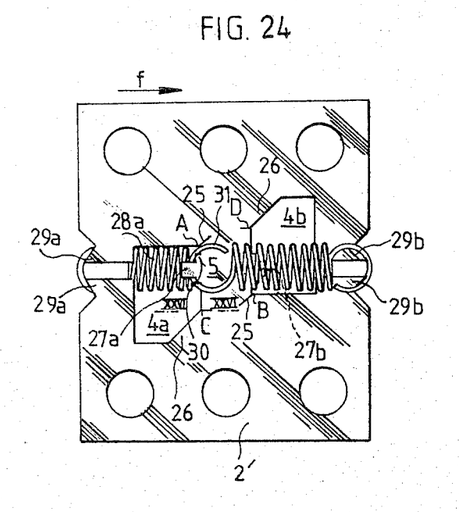
FIG. 24 is an elevation of a another embodiment of fatigue damage indicator.
Figure 25:
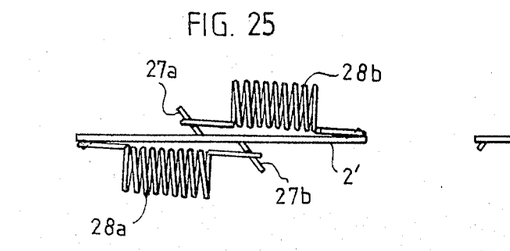
FIG. 25 is plan view of the embodiment of FIG. 24.

In FIG. 24, a fatigue indicator is shown which is similar to that of FIG. 21, that is to say it comprises a thin plate 2' intended to be secured to portions of the part of which the fatigue stress is to be monitored. This securing is effected in such a manner that when the part is working a portion of the plate, which is the upper part of FIG. 24, moves from the left to the right in this Figure as indicated by the arrow f.

The blind end of the left-hand slot 4a is chamfered as indicated at 26, while the blind end of the slot 4b comprises a similar chamfer 26 at its upper edge. When the part is working, cracks tend to be produced at the angles A and B which are compressed and at angles C and D which are extended. Owing to the chamfer 26, the angles C and D are obtuse, which slows up the formation of the cracks and counterbalances the fact that the cracks commence and propagate more readily at the extended angles than at the compressed angles. The formation of cracks is better balanced and the cracks begin practically simultaneously at the four angles A,B,C,D of the two slots 4a, 4b. If desired, it is possible to form the notches 25 which start from angles A,B,C and D and extend outwardly of the slots, obliquely to the notches which extend from the obtuse angles A and B parallel to the notches which extend from the angles C and D.

The blind end of each of the slots 4a, 4b comprises a tab 27a or 27b, respectively, which is extended outwardly from the plane of the thin plate 2', one on one side of this plane and the other on the opposite side. Each of these two tabs is intended for anchoring of one of the ends of a spring 28a, 28b. The other end of the spring can be secured to the part from which the fatigue is to be monitored. But, in the embodiment shown, it is secured to two lugs 29a, 29b, respectively, which project inwardly from the slots 4a and 4b.

Figure 27:
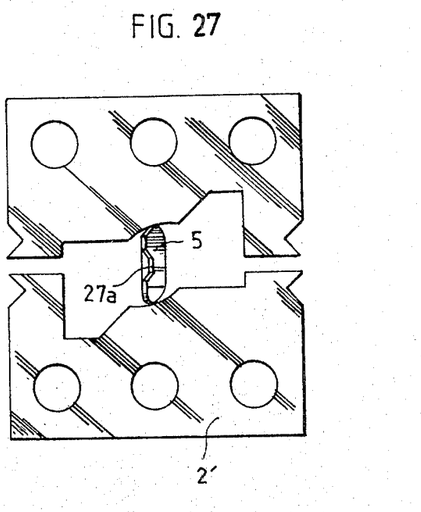
FIGS. 27 and 28 are similar views to FIGS. 24 and 25 showing the part fatigued.
Figure 28:
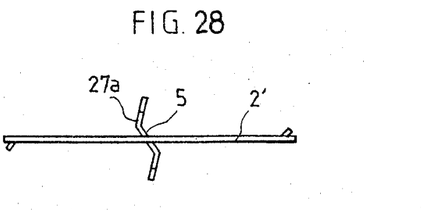

The springs 28a and 28b exert a moment on the central part 5 lying between the slots 4a and 4b. When the part is fatigued and the cracks start at the angles A,B,C and D (or notches 25 if they are provided), and are on the point of meeting in pairs, this moment causes the part 5 to pivot, as shown in FIG. 27. If the material of the plate is not very ductile, or there is a fracture at the ends of the cracks, the central part 5 is automatically ejected. If the material is more ductile it may be that the part 5 will remain in the position of FIGS. 27 and 28, but the pivot action indicates that the part is fatigued.

As will be apparent more particularly in FIG. 24, each of the tabs 27a and 27b comprises a shoulder 30 which serves for an abutment of an anchoring loop 31 for the spring. The latter has a predetermined position on the tab so that the moment, which tends to cause pivoting of the central part 5, will have a precise value.

Figure 26:
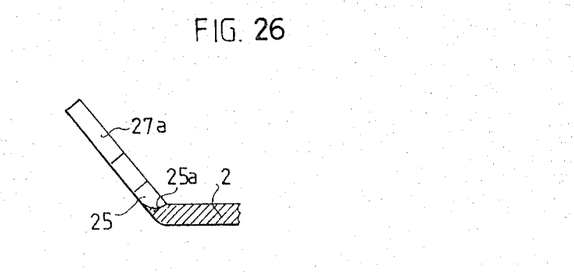
FIG. 26 is a section taken on the line XXVI—XXVI of FIG. 24.

As it can be seen more particularly in FIG. 26, the front face 25a of the notch 25 has the shape of an inclined chamfer with respect to the plane of the plate, owing to the upstanding nature of the tab 27a. This chamfer facilitates the initiation of the crack starting from the notch.

Figure 29:
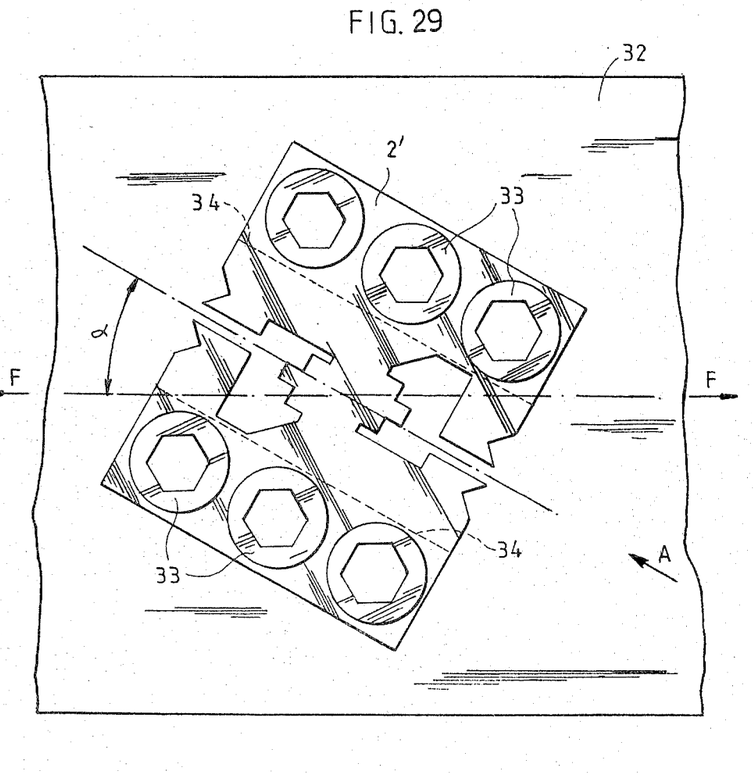
FIG. 29 is an elevational view of another embodiment of a fatigue indicator.
Figure 30:
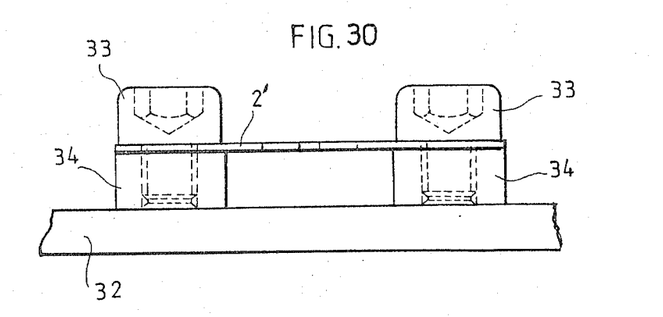
FIG. 30 is a view taken in the direction of arrow A of FIG. 29.

In the embodiment of FIGS. 29 and 30, the fatigue indicator comprises a plate 2' which is similar to that shown in FIG. 1 and is secured on the part 32 to be monitored by pins 33, with the interposition of blocks 34 and slots 4a and 4b forming an angle α of the order of 29° with the direction F of the main stress to which part 32 is submitted.

Under these conditions, the movement of the two parts of the plate 2', disposed on either side of the axis of the slots 4a and 4b, is practically pure sliding.

I claim:

1. A fatigue damage indicator comprising:
   a first comparatively thick member;
   a second comparatively thick member; and
   a comparatively thin plate interconnecting the first and second thick members so disposed that stresses applied to the first and second members are applied to the thin plate as a shear stress, and having two slots each extending in the direction of applied stress to the first and second members, a predetermined fatigue stress serving to crack the comparatively thin plate starting from the slots and displace a part thereof from its initial location relative to the first and second members, the thin plate comprising respective tabs upstanding from the thin plate at the blind ends of said slots.

2. A fatigue damage indicator comprising:
   a first comparatively thick member;
   a second comparatively thick member; and
   a comparatively thin plate interconnecting the first and second thick members so disposed that stresses applied to the first and second members are applied to the thin plate as a shear stress, and having two slots each extending in the direction of applied stress to the first and second members, a predetermined fatigue stress serving to crack the comparatively thin plate starting from the slots and displace a part thereof from its initial location relative to the first and second members, the thin plate having grooves formed on at least one face, each groove starting from a corner of the blind end of the respective slot.

3. A fatigue damage indicator comprising:
   a first comparatively thick member;
   a second comparatively thick member; and
   a comparatively thin plate interconnecting the first and second thick members so disposed that stresses applied to the first and second members are applied to the thin plate as a shear stress, and having two slots each extending in the direction of applied stress to the first and second members, a predetermined fatigue stress serving to crack the comparatively thin plate starting from the slots and displace a part thereof from its initial location relative to the first and second members, notches being formed in the plate starting at the blind end of the slots.

4. An indicator according to claim 3, wherein the front face of each notch is chamfered and inclined with respect to the plane of the thin plate.

5. A fatigue damage indicator comprising:
   a first comparatively thick member;
   a second comparatively thick member;
   a comparatively thin plate interconnecting the first and second thick members so disposed that stresses applied to the first and second members are applied to the thin plate as a shear stress, and having two slots each extending in the direction of applied stress to the first and second members, a predetermined fatigue stress serving to crack the comparatively thin plate starting from the slots and displace a part thereof from its initial location relative to the first and second members, the thin plate comprising a tab upstanding therefrom at the blind ends of the slots, and a tension spring one end of which is mounted on the tab and the other end of which is adapted to be mounted on the part to be monitored.

6. An indicator according to claim 5, wherein the tab has a shoulder forming an abutment for the spring and determining its position with respect to the plane of the plate.

7. In a fatigue damage indicator for a mechanical member subjected to repetitive stress, comprising two thick elements which are spaced from one another and are connected one to the other by a thin plate formed with a slot and at least a pair of free opposite edges, the two elements being so connected with the mechanical member of fixed to the latter so that they are displaceable relative to one another in a plane parallel to the plane of the thin plate, the improvement wherein the thick elements are disposed so as to be separated from one another in a direction substantially perpendicular to their direction of relative displacement by such stress, the thin plate being placed under shear force in its plane by such relative displacement, the slot of the thin plate extending from one of the edges of the thin plate in the said direction of relative displacement and terminating short of the opposite edge in a blind end of the slot having two corners so that with application of stress two cracks develop at corners of the bottom of the slot and are propagated progressively in the thin plate toward an opposite edge of the thin plate so that said cracks meet cracks propagating generally in a direction away from said opposite edge to detach a central zone of the thin plate delimited by said cracks.

8. The improvement defined in claim 7 wherein the two thick elements and the thin plate are formed unitarily from a single piece provided with circular bores extending into said piece from opposite sides and terminating short of one another to define said thin plate between them.

9. The improvement defined in claim 7 wherein said thin plate is circular.

10. The improvement defined in claim 7 wherein said thin plate is provided with a central hole.

11. The improvement defined in claim 7 wherein two such slots are provided generally opposite one another in the direction of relative displacement of the two thick elements in said thin plate.

12. The improvement defined in claim 7 wherein said blind end of the slot is planar.

13. The improvement defined in claim 7 wherein the thick elements are so secured to said mechanical member that the longitudinal direction of each of said elements forms an angle of substantially 25° to 35° with the direction of applied stress on said thin plate.

* * * * *